United States Patent [19]

Sarpeshkar et al.

[11] Patent Number: 5,346,981
[45] Date of Patent: Sep. 13, 1994

[54] RADIOPAQUE POLYURETHANES

[75] Inventors: Ashok M. Sarpeshkar, Upper St. Clair; Peter H. Markusch, McMurray, both of Pa.

[73] Assignee: Miles Inc., Pittsburgh, Pa.

[21] Appl. No.: 3,755

[22] Filed: Jan. 13, 1993

[51] Int. Cl.$^5$ ............................................. C08G 18/32
[52] U.S. Cl. ........................................ 528/85; 528/76; 528/77; 528/86; 528/271; 528/272; 528/299
[58] Field of Search .................. 528/76, 77, 85, 86, 528/271, 272, 299

[56] References Cited

U.S. PATENT DOCUMENTS

| | | | |
|---|---|---|---|
| 2,212,334 | 8/1936 | Wallerich | 18/58 |
| 2,857,915 | 10/1958 | Sheridan | 128/349 |
| 3,336,918 | 8/1967 | Jeckel | 128/2.05 |
| 3,529,633 | 10/1967 | Vaillancourt | 138/118 |
| 3,605,750 | 9/1971 | Sheridan et al. | 128/348 |
| 3,608,555 | 9/1971 | Greyson | 128/348 |
| 3,618,614 | 11/1971 | Flynn | 128/348 |
| 3,645,955 | 2/1972 | Flynn | 260/31.4 |
| 3,749,134 | 7/1973 | Slingluff et al. | 138/177 |
| 3,901,829 | 8/1975 | Slingluff et al. | 252/478 |
| 4,027,659 | 6/1977 | Slingluff | 128/2 M |
| 4,105,732 | 8/1978 | Slingluff | 264/104 |
| 4,182,787 | 1/1980 | Goossens et al. | 428/36 |
| 4,282,876 | 8/1981 | Flynn | 128/349 R |
| 4,722,344 | 2/1988 | Cambon et al. | 128/658 |
| 4,939,007 | 7/1990 | Hu et al. | 428/341 |
| 5,177,170 | 1/1993 | Sarpeshkar et al. | 528/76 |

OTHER PUBLICATIONS

Y. Delaviz et al, Polymer Preprints (Polymer Division, Am. Chem. Soc.), 30, 215–216 (1989).

*Primary Examiner*—John Kight, III
*Assistant Examiner*—Duc Truong
*Attorney, Agent, or Firm*—Joseph C. Gil; Richard E. L. Henderson

[57] ABSTRACT

This invention relates to radiopaque polyurethane compositions that are reaction products of
 (a) cycloaliphatic diisocyanates;
 (b) at least one polyester, polycarbonate, and/or polyester carbonate diol having a molecular weight of from about 1000 to about 6000;
 (c) an isocyanate-reactive bromine-containing aromatic chain extender; and
 (d) optionally, a catalyst;
wherein the quantity of component (c) is such that the amount of bromine in the polyurethane composition is from 10 to 35% by weight, and wherein the components are reacted at an isocyanate index of from 0.95 to 1.2.

8 Claims, No Drawings

RADIOPAQUE POLYURETHANES

BACKGROUND OF THE INVENTION

This invention relates to radiopaque polyurethane compositions having a bromine content of from 10 to 35% by weight prepared by the reaction of cycloaliphatic diisocyanates, certain polyester diols, and a sufficient amount of a bromine-containing aromatic chain extender to provide the required bromine content.

When medical or veterinary devices are inserted or implanted in a subject, it is often desirable to be able to locate them by X-ray examination, particularly when catheters or cannulas are being inserted into body cavities, passages, or vessels. It is also often desirable, especially with catheters, to observe visually fluids within exposed portions of such devices.

Consequently, an object of the present invention is to prepare radiopaque polyurethane compositions that are preferably optically transparent.

Several approaches for achieving this object in catheters have been reported. For example, U.S. Pat. No. 2,212,334 discloses the incorporation of short segments of radiopaque material within otherwise transparent tubes by introduction of such material at regular intervals during manufacture of the catheters. Alternatively, U.S. Pat. Nos. 2,857,915, 4,027,659, and 4,105,732 disclose the introduction of the radiopaque material as continuous stripes running the length of the catheters. It is also possible to include a radiopaque material only at the distal end of the catheter, as disclosed in U.S. Pat. No. 3,605,750, but the intervening portion of the catheter is not readily detectable by X-ray examination. Similarly, U.S. Pat. No. 3,529,633 discloses catheters made primarily from polymers that are opaque to both X-rays and visible light but also have small sections made from transparent materials.

Another variant of this approach is described in U.S. Pat. No. 3,618,614, which discloses a multiwall tubing having a thick transparent inner tube encased within a thin transparent tube containing a radiopaque material. In this variant, the relatively longer path-length through edges of the tube provides sufficient contrast to appear during X-ray examination. U.S. Pat. No. 3,336,918 discloses similar effects obtained by incorporating metal powders into polyurethane coatings.

Yet another approach is to disperse X-ray opaque substances, such as barium sulfate, a bismuth halide, or a halogen-containing plasticizer, diol, or other such halogen-containing material, throughout a visually transparent polymer. See, for example, Y. Delaviz et al., *Polymer Preprints* (Polymer Division, Am. Chem. Soc.), 30, 215-216 (1989), and U.S. Pat. Nos. 3,608,555, 3,645,955, 3,749,134, 3,901,829, and 4,282,876. Blends of polymers, at least one of which is radiopaque, are reported, for example, in U.S. Pat. No. 4,182,787, to provide similar effects. Each of these approaches, however, involves the use of physical blends, at least some of which have inherent disadvantages. For example, some of the radiopaque substances can be leached out of the polymeric substrate and absorbed by the body. In addition, some additives can have other incompatibilities that make them unsuitable for use in humans or animals.

It would be particularly advantageous to make the medical or veterinary devices from a polymeric material in which the radiopaque component is incorporated as a structural unit of the polymer. For example, U.S. Pat. No. 4,722,344, which is incorporated by reference, discloses polyurethanes prepared using halogenated polyols and/or halogenated polyisocyanates as reactants. Although the polyurethanes disclosed in U.S. Pat. No. 4,722,344 incorporate sufficient bromine to provide the desired radiopacity, these polyurethanes have a high flex modulus but do not exhibit the desirable softening effect in saline solutions (which are used in testing as a substitute for blood).

Optically transparent radiopaque polyurethanes that are dimensionally stable under standard sterilization conditions (for example, ethylene oxide treatment or gamma irradiation) would be desirable. This stability can be achieved by using crystalline building blocks. For example, polyester diols based on adipic acid and $C_4$-$C_8$ alkanediols can provide elastomers having enhanced crystallinity. Aromatic chain extenders can further enhance polymer crystallinity. It is possible to make radiopaque polyurethanes based on cycloaliphatic diisocyanates, polyester diols, and isocyanate-reactive bromine-containing compounds, but polyester-polyurethanes of this type that are both radiopaque and optically transparent have not previously been reported.

Soft optically transparent radiopaque polyurethanes have been disclosed in U.S. Pat. No. 5,177,170 but the disclosed polyurethanes are based on polyethers and certain aliphatic bromine-containing chain extenders rather than on the polyester and/or polycarbonate polyols and aromatic bromine-containing chain extenders of the present invention.

It was, therefore, an object of the present invention to obtain radiopaque polyurethanes (preferably optically transparent polyurethanes) having high halogen content that are normally hard and elastic but which soften upon exposure to blood or saline solutions. This object has been accomplished by using polyols containing ester and/or carbonate groups and partially or completely replacing the previously reported brominated chain extenders with isocyanate-reactive bromine-containing aromatic chain extenders such as tetrabromobisphenol A bis(2-hydroxyethyl ether).

SUMMARY OF THE INVENTION

This invention relates to a radiopaque polyurethane composition comprising a reaction product of
(a) a cycloaliphatic diisocyanate;
(b) at least one polyester, polycarbonate, and/or polyester carbonate diol having a molecular weight of from about 1000 to about 6000;
(c) an isocyanate-reactive bromine-containing aromatic chain extender (preferably tetrabromobisphenol A bis(2-hydroxyethyl ether)); and
(d) optionally, a catalyst;

wherein the quantity of component (c) is such that the amount of bromine in the polyurethane composition is from about 10 to about 35% by weight (preferably from 20 to 30% by weight), and wherein the components are reacted at an isocyanate index of from about 0.95 to about 1.2.

DETAILED DESCRIPTION OF THE INVENTION

Suitable diisocyanates for preparing the polyurethane compositions of the invention are those containing one or more cycloaliphatic hydrocarbon groups containing 4 to about 15 (preferably 5 to 10) carbon atoms. Examples of suitable such cycloaliphatic diisocyanates include cyclobutane-1,3-diisocyanate, cyclohexane-1,3- and -1,4-diisocyanate and mixtures thereof, 1-isocyanato-3,3,5-trimethyl-5-isocyanatomethylcyclohexane (isophorone diisocyanate), 2,4- and 2,6-hexahydrotoluene diisocyanate and mixtures thereof, and dicyclohexylmethane-4,4'-diisocyanate ("hydrogenated MDI", or "HMDI"). Dicyclohexylmethane-4,4'-diisocyanate is particularly preferred.

Suitable hydroxyl-containing polyesters include reaction products of polyhydric alcohols (preferably diols), optionally with the addition of trihydric alcohols, and polybasic (preferably dibasic) carboxylic acids and have a molecular weight of from about 1000 to about 6000. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic, or heterocyclic and may be substituted, e.g., by halogen atoms, and/or unsaturated. Suitable polycarboxylic acids include succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endo-methylene tetrahydrophthalic acid anhydride, glutaric acid anhydride, maleic acid, maleic acid anhydride, fumaric acid, dimeric and trimeric fatty acids, dimethyl terephthalic, and terephthalic acid bis-glycol esters. Suitable polyhydric alcohols include ethylene glycol, 1,2- and 1,3-propanediol, 1,4- and 2,3-butanediol, 1,6-hexanediol, 1,8-octanediol, neopentyl glycol, 1,3-and 1,4-bis(hydroxymethyl)cyclohexane, 2-methyl-1,3-propanediol, glycerol, trimethylolpropane, 1,2,6-hexanetriol, 1,2,4-butanetriol, trimethylolethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutylene glycol, and polybutylene glycols. The polyesters may also contain a proportion of carboxyl end groups. Polyesters of lactones, such as ε-caprolactone, or of hydroxycarboxylic acids, such as ω-hydroxycaproic acid, may also be used. Hydrolytically stable polyesters are preferably used in order to obtain the greatest benefit relative to the hydrolytic stability of the final product. Preferred polyesters include polyesters of adipic acid and straight chained or branched $C_4$-$C_8$ diols, most preferably a polybutylene adipate having a molecular weight of from 2000 to 4000.

Suitable polycarbonates include those prepared by the reaction of diols, such as 1,3-propanediol, 1,4-butanediol, 1,6-hexanediol, diethylene glycol, triethylene glycol, tetraethylene glycol, or thiodiglycol, with phosgene or diaryl carbonates such as diphenyl carbonate. E.g., German Auslegeschriften 1,694,080, 1,915,908, and 2,221,751; German Offenlegungsschrift 2,605,024.

Suitable polyester carbonates include those prepared by the reaction of polyester diols, with or without other diols such as 1,3-propanediol, 1,4-butanediol, 1,6-hexanediol, diethylene glycol, triethylene glycol, tetraethylene glycol, or thiodiglycol, with phosgene, cyclic carbonates, or diaryl carbonates such as diphenyl carbonate. Suitable polyester carbonates more generally include compounds such as those disclosed in U.S. Pat. No. 4,430,484.

Any mixtures of the above-mentioned polyesters, polycarbonates, and polyester carbonates are, of course, also suitable.

The brominated chain extender is an isocyanate-reactive bromine-containing aromatic chain extender, including, for example, compounds having the formulas

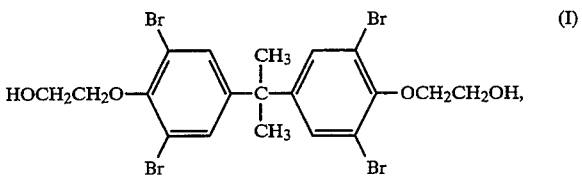

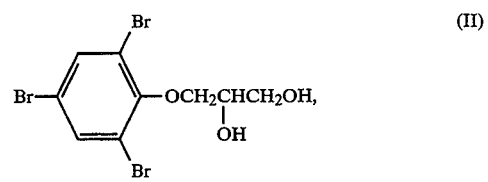

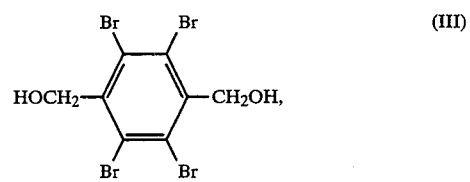

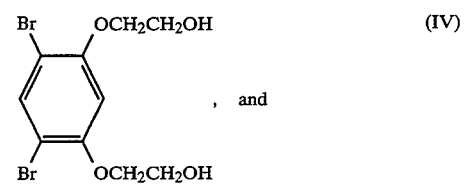

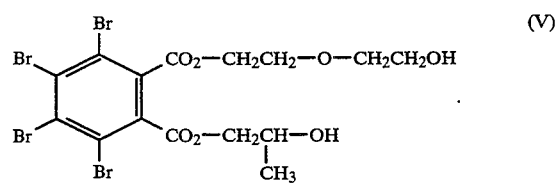

Each of the illustrative bromine-containing chain extenders is available commercially or can be prepared by methods known in the art. It is also possible, although not preferred, to use other brominated chain extenders known in the art. A preferred chain extender is tetrabromobisphenol A bis(2-hydroxyethyl ether) (that is, the chain extender of formula (I)), which is available commercially from Great Lakes Chemical Corporation. See also E. R. Larsen, "Halogenated Flame Retardants" in *Kirk-Othmer Encyclopedia of Chemical Technology*, Third Edition, Vol. 10 (New York: John Wiley & Sons, 1980), pages 373–395. A mixture containing more than one brominated chain extender can, of course, be used.

The brominated chain extender is used in a quantity such that the amount of bromine is sufficient to render the polyurethane radiopaque. The term "radiopaque" refers to the property of polyurethane compositions of the invention that allows articles prepared from such compositions to be detected by customary X-ray examination procedures after insertion into the patient. It has been found that a bromine content of at least about 10 to 15% by weight of polyurethane is generally sufficient to provide radiopacity. In addition to exhibiting excellent radiopacity, the preferred polyurethane compositions of the invention are optically transparent. The term "optically transparent" refers to the property of polyurethane compositions of the invention that allows normal visual observation into or through articles prepared from such compositions. For example, blood or other fluids contained in flowing through an optically transparent catheter can be observed from outside the catheter under normal illumination. Although a bromine content of at least about 10 to 15% by weight is sufficient to confer radiopacity, it has been found that a bromine content of less than about 20% by weight (depending on the particular brominated chain extender used) may result in an optically opaque or translucent polyurethane.

The specified bromine content of 10 to 35% by weight can be obtained by using the polyester diol component (b) and the brominated chain extender component (c) in quantities such that the weight ratio of the polyether diol to the brominated chain extender is from about 2:98 to about 76:24. The corresponding weight ratio for the preferred range of 20 to 30% by weight bromine is about 19:81 to about 50:50.

Suitable catalysts can be any of the catalysts normally used for the preparation of polyurethanes. Preferred catalysts include the organic metal compounds, especially organic tin compounds. Suitable organic tin compounds include those containing sulfur, such as dioctyl tin mercaptide (German Auslegeschrift 1,769,367 and U.S. Pat. No. 3,645,927), and, preferably, tin(II) salts of carboxylic acids, such as tin(II) acetate, tin (II) octoate, tin(II) ethylhexoate, and tin(II) laurate, as well as tin-(IV) compounds, such as dibutyltin dilaurate.

Suitable but less preferred catalysts include tertiary amines such as triethylamine, tributylamine, N-methylmorpholine, N-ethylmorpholine, N,N,N',N'-tetramethylethylene diamine, pentamethyldiethylene triamine, and higher homologs (German Offenlegungsschriften 2,624,527 and 2,624,528), 1,4-diazabicyclo[2.2.2]octane, N-methyl-N'-(dimethylaminoethyl)piperazine, bis(dimethylaminoalkyl)piperazines (German Offenlegungsschrift 2,636,787), N,N-dimethylbenzylamine, N,N-dimethylcyclohexylamine, N,N-diethylbenzylamine, bis(N,N-diethylaminoethyl) adipate, N,N,N',N'-tetramethyl-1,3-butanediamine, N,N-dimethyl-$\beta$-phenylethylamine, 1,2-dimethylimidazole, 2-methylimidazole, monocyclic and bicyclic amidines (German Offenlegungsschrift 1,720,633), bis(dialkylamino)alkyl ethers (U.S. Pat. No. 3,330,782, German Auslegeschrift 030,558, and German Offenlegungsschriften 1,804,361 and 2,618,280), and tertiary amines containing amide groups (preferably formamide groups) according to German Offenlegungsschriften 2,523,633 and 2,732,292. The catalysts used may also be the known Mannich bases of secondary amines (such as dimethylamine) and aldehydes (preferably formaldehyde) or ketones (such as acetone) and phenols.

Any of the above-mentioned catalysts may, of course, be used as mixtures.

The catalysts can be premixed with the diisocyanate component, the polyether diol component, or, less preferably because of potential side reactions, the brominated chain extender, or they can be added separately. Catalysts, if used at all, are generally used in a quantity ranging from about 0.001 to about 1% by weight of the total reaction mixture, although about 0.01 to 0.1 percent by weight is generally preferred.

Auxiliary agents and additives other than catalysts may optionally also be used in the preparation of the compounds of the invention. Suitable auxiliary agents and additives may include, for example, internal mold release agents, processing aids, antioxidants, plasticizers, and fungistatic or bacteriostatic substances. The auxiliaries and additives can be used in quantities normally used for such materials. For example, when using the preferred antioxidants and processing aids, it is generally preferred, although not critical, to use about 0.1 to 1.5 percent by weight of the antioxidant and about 0.15 to 1.0 percent by weight of the processing aid.

The polyurethane compositions are prepared by any of several methods known in the art. The polyurethane-forming reaction components may be reacted by the known one-stage process, by the prepolymer process, or by the semi-prepolymer process. Machines, such as those described in U.S. Pat. No. 2,764,565, may be used in many of these processes. Particulars of the processing machines which may also be used to produce polyurethanes according to the invention may be found in Kunststoff-Handbuch, Vol. VII, Vieweg and Höchtlen, Carl-Hanser-Verlag, Munich 1966, pages 121 to 205.

In the one-stage (or "one-shot") method, the isocyanate-reactive components, including the polyester diol and the isocyanate-reactive bromine-containing compound, as well as any additives and auxiliaries, are combined and thoroughly blended in a premix. The cycloaliphatic diisocyanate is then mixed with the premix. The isocyanate-reactive and diisocyanate components can be mixed batchwise or in a processing machine and poured into a mold or can be introduced separately into a mold where the polymerization reaction takes place. External release agents, such as silicone oils, are often used during the molding process. It is, however, also possible to use so-called "internal release agents", optionally in admixture with external release agents, as described, for example, in German Offenlegungsschriften 2,121,670 and 2,307,589.

In the prepolymer method, a prepolymer is formed by reacting the diisocyanate with a portion of the polyester diol or a blend of the polyester diol with the bromine-containing compound. The prepolymer is then allowed to react with the balance of the isocyanate-reactive components to form a polyurethane composition of the invention.

The semiprepolymer method is similar to the prepolymer method except that a portion of the cycloalkyl diisocyanate remains unreacted. That is, the isocyanate component is a mixture of unreacted diisocyanate and true prepolymer. As in the prepolymer method, the semiprepolymer is then allowed to react with the balance of the isocyanate-reactive components to form a polyurethane.

Regardless of the method used, the reactive components are used in quantities such that the isocyanate index is from about 0.95 to about 1.2 (preferably 0.95 to 1.1). By "isocyanate index" is meant the quotient of the number of isocyanate groups divided by the number of isocyanate-reactive groups.

The radiopaque thermoplastic polyurethanes of the invention may be processed by melt processing techniques known in the art. For example, slabs of the polyurethane can be chopped into strips and further granulated into smaller pieces. After being dried in a vacuum oven, the resultant ground material can be melt extruded on a single screw or twin screw extruder into strands that are then pelletized. In contrast to aromatic polyisocyanate-based thermoplastic polyurethanes that are melt extruded at temperatures of about 175° C. to 400° C., polyurethanes of the present invention can be successfully melt extruded at much lower temperatures, for example, as low as about 90° C. (preferably 90° C. to 200° C.). The pelletized material may then be subjected to a second melt processing step to produce the desired articles. Thus, the polyurethanes of the invention may be extruded into tubes and catheters of various internal and external diameters and gauges. Furthermore, they may be again extruded, co-extruded with other polymers, or injection molded into virtually any desired shape.

The following examples further illustrate details for the preparation of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Starting materials

Isocyanate—dicyclohexylmethane-4,4'-diisocyanate (available as DESMODUR W from Miles Inc.)

Polyol—a polybutylene adipate having a molecular weight of from 2000 to 4000 (available as DESMOPHEN 2502 from Miles Inc.)

Extender—tetrabromobisphenol A bis(2-hydroxyethyl ether) (available as BA-50P from Great Lakes Chemical Corporation)

Catalyst—dibutyltin dilaurate (available as DABCO T-12 from Air Products and Chemicals, Inc.)

Antioxidant—octadecyl 3,5-di-t-butyl-4-hydroxycinnamate (available as IRGONOX 1076 from Ciba-Geigy)

Processing aid—N,N-dioleoylethylenediamine (available as GLYCOLUBE VL from Lonza)

General Procedure

Each example was carried out using 0.02 wt. % catalyst, 1.0 wt.% antioxidant, and 0.55 wt. % processing aid based on the total reaction mixture. Proportions of the reactive isocyanate, polyol, and extender components (given as equivalent ratios relative to the isocyanate), as well as hard segment and bromine content of the resultant polyurethanes, are listed in Table 1.

The polyester polyol, bromine-containing chain extender, antioxidant, and processing aid were mixed in a stainless steel reactor, which was then placed in a convection oven at a temperature of about 80°-130° C. until a molten liquid mixture was obtained (typically about two hours). The isocyanate and catalyst were added to a dry container and warmed in an oven at about 60° C. until used.

The molten polyol component was then vigorously stirred with a high speed homogenizer and maintained at a temperature of about 100° C. The isocyanate component was then added in one portion to the reactor. The resultant mixture was stirred for about 15 seconds, after which it was poured into a teflon-lined tray and post-cured in an infrared oven for five minutes at 120° C. and an additional five minutes at 90° C. The molded material was removed from the oven and allowed to cool to 25° C.

The resultant slab was granulated and dried in a vacuum oven at a temperature below 60° C. for about 16 hours. The dried granulate was then processed using a single-screw extruder at temperatures of 120°-180° C. to give optically transparent strands of polyurethane product. The temperatures used for extrusion of the Examples are listed in Table 1.

The strands were then pelletized. The pelletized polyurethane was injection molded at about the same temperatures as used for the extrusions to form plaques having a thickness of 3.175 mm. Physical properties of the polyurethane plaques are listed in Table 2.

TABLE 1

Compositions and extrusion temperatures used for polyurethanes of the invention

| | Example 1 | Example 2 |
|---|---|---|
| Polyol (equiv. ratio[1]) | 0.105 | 0.184 |
| Extender (equiv. ratio[2]) | 0.86 | 0.78 |
| Hard segment (wt. %) | 65.33 | 67.56 |
| Bromine content (wt. %) | 22.10 | 22.10 |
| Extrusion temperature (°C.) | 149-171 | 154-169 |

[1]Equivalent ratio of polyol to isocyanate
[2]Equivalent ratio of extender to isocyanate

TABLE 2

Physical properties of polyurethane plaques of the invention

| | Example 1 | Example 2 |
|---|---|---|
| Elongation (MPa) | 2.28 | 2.31 |
| Tensile strength (break) (MPa) | 21.31 | 32.55 |
| Modulus (MPa) | | |
| At 100% | 13.86 | 22.78 |
| At 200% | 15.17 | 23.45 |
| At 300% | 19.21 | 29.99 |
| Flex modulus (MPa) | | |
| Dry | 273.48 | 784.67 |
| Wet (24 hr) | 156.88 | 386.72 |
| Shore D hardness | 65 | 75 |

What is claimed:

1. An optically clear radiopaque polyurethane composition comprising a reaction product of
   (a) a cycloaliphatic diisocyanate;
   (b) at least one polyester diol having a molecular weight of from about 1000 to about 6000;
   (c) an isocyanate-reactive bromine-containing aromatic chain extender; and
   (d) optionally, a catalyst;

wherein the quantity of component (c) is such that the amount of bromine in the polyurethane composition is from 20 to 30% by weight, and wherein the components are reacted at an isocyanate index of from 0.95 to 1.2.

2. An optically clear, radiopaque polyurethane composition according to claim 1 wherein the cycloaliphatic diisocyanate is dicyclohexylmethane-4,4'-diisocyanate.

3. An optically clear, radiopaque polyurethane composition according to claim 1 wherein component (b) is a polyester diol consisting of a condensation product of adipic acid and a $C_4$-$C_8$ alkanediol.

4. An optically clear, radiopaque polyurethane composition according to claim 1 wherein component (b) is a polyester diol having a molecular weight of from 2000 to 4000.

5. An optically clear, radiopaque polyurethane composition according to claim 1 wherein component (b) is a polyester diol consisting of a polybutylene adipate having a molecular weight of from 2000 to 4000.

6. An optically clear, radiopaque polyurethane composition according to claim 1 wherein the isocyanate-reactive bromine-containing aromatic chain extender is tetrabromobisphenol A bis(2-hydroxyethyl ether).

7. An optically clear, radiopaque polyurethane composition comprising a reaction product of
 (a) dicyclohexylmethane-4,4'-diisocyanate;
 (b) a polybutylene adipate having a molecular weight of from 2000 to 4000;
 (c) tetrabromobisphenol A bis(2-hydroxyethyl ether) as chain extender; and
 (d) optionally, a catalyst;
wherein the quantity of component (c) is such that the amount of bromine in the polyurethane composition is from 20 to 30% by weight, and wherein the components are reacted at an isocyanate index of from 0.95 to 1.2.

8. An optically clear, radiopaque polyurethane composition according to claim 1 prepared by melt processing.

* * * * *